(12) United States Patent
Sauers

(10) Patent No.: US 8,721,850 B2
(45) Date of Patent: May 13, 2014

(54) BIOSENSOR AND METHODS FOR MANUFACTURING

(75) Inventor: Matthew Carlyle Sauers, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 789 days.

(21) Appl. No.: 12/698,245

(22) Filed: Feb. 2, 2010

(65) Prior Publication Data

US 2011/0186430 A1    Aug. 4, 2011

(51) Int. Cl.
*C12M 1/00* (2006.01)
*G01N 1/00* (2006.01)
*G01N 31/00* (2006.01)
*C12Q 1/00* (2006.01)

(52) U.S. Cl.
USPC ............... 204/403.01; 204/400; 204/403.4; 204/403.14; 205/775; 205/777.5

(58) Field of Classification Search
USPC ............ 204/403.01–403.15; 205/775, 777.5; 600/372, 373
See application file for complete search history.

(56) References Cited

U.S. PATENT DOCUMENTS

| | | | |
|---|---|---|---|
| 4,330,349 A | 5/1982 | Swift et al. | |
| 4,702,815 A | 10/1987 | Prestridge et al. | |
| 4,737,257 A | 4/1988 | Boulton | |
| 4,841,099 A | 6/1989 | Epstein et al. | |
| 4,970,553 A | 11/1990 | Orlowski et al. | |
| 5,139,862 A | 8/1992 | Swift et al. | |
| 5,167,512 A | 12/1992 | Walkup | |
| 5,220,481 A | 6/1993 | Swift et al. | |
| 5,250,756 A | 10/1993 | Swift et al. | |
| 5,267,866 A | 12/1993 | Swift et al. | |
| 5,269,891 A * | 12/1993 | Colin | 205/777.5 |
| 5,270,106 A | 12/1993 | Orlowski et al. | |
| 5,281,771 A | 1/1994 | Swift et al. | |
| 5,354,607 A | 10/1994 | Swift et al. | |
| 5,366,773 A | 11/1994 | Schroll et al. | |
| 5,410,386 A | 4/1995 | Swift et al. | |
| 5,414,216 A | 5/1995 | Swift et al. | |
| 5,420,465 A | 5/1995 | Wallace et al. | |
| 5,492,743 A | 2/1996 | Schroll et al. | |
| 5,522,977 A * | 6/1996 | Shieh | 204/403.06 |
| 5,599,615 A | 2/1997 | Swift et al. | |

(Continued)

FOREIGN PATENT DOCUMENTS

EP    0 136 362 A1    4/1985
EP    1 672 364 A1    6/2006

(Continued)

*Primary Examiner* — Luan Van
*Assistant Examiner* — Maris R Kessel
(74) *Attorney, Agent, or Firm* — Woodard, Emhardt, Moriarty, McNett & Henry LLP (57) ABSTRACT

A biosensor for detecting an analyte in a sample of body fluid and methods for manufacturing the biosensor are disclosed. In one embodiment, a biosensor includes at least two electrical conductors embedded within an electrically insulating test element body. The electrical conductors are exposed at two ends of the test element body and a reagent, for example a reagent adapted to test for blood glucose, is applied to one end. In one form, the test element body is cylindrical with a circular or non-circular cross-sectional shape. In other embodiments, the test elements are manufactured by a resin pultrusion process in which resin embedded with electrical conductors is dried or cured, shaped and cut into segments, and reagent applied to one end of each segment.

27 Claims, 7 Drawing Sheets

(56) References Cited

U.S. PATENT DOCUMENTS

| | | | |
|---|---|---|---|
| 5,689,791 A | 11/1997 | Swift | |
| 5,744,090 A | 4/1998 | Jones et al. | |
| 5,756,998 A | 5/1998 | Marks et al. | |
| 5,794,100 A | 8/1998 | Bell et al. | |
| 5,812,908 A | 9/1998 | Larocca et al. | |
| 5,843,567 A | 12/1998 | Swift et al. | |
| 6,214,921 B1 | 4/2001 | Bluett et al. | |
| 6,217,341 B1 | 4/2001 | Glick et al. | |
| 6,265,046 B1 | 7/2001 | Swift | |
| 6,289,187 B1 | 9/2001 | Swift et al. | |
| 7,052,763 B2 | 5/2006 | Swift et al. | |
| 7,754,152 B2 | 7/2010 | Riebel et al. | |
| 2002/0046721 A1 | 4/2002 | Lee | |
| 2003/0212345 A1* | 11/2003 | McAllister et al. | 600/584 |
| 2004/0184954 A1 | 9/2004 | Guo et al. | |
| 2005/0258050 A1* | 11/2005 | Harding | 205/775 |
| 2006/0011474 A1 | 1/2006 | Schulein et al. | |
| 2006/0116755 A1 | 6/2006 | Stinson | |
| 2007/0229099 A1 | 10/2007 | Campbell et al. | |
| 2008/0159913 A1* | 7/2008 | Jung et al. | 422/57 |
| 2010/0236941 A1 | 9/2010 | Riebel et al. | |
| 2011/0189762 A1* | 8/2011 | Say | 435/287.1 |
| 2011/0203941 A1* | 8/2011 | Say | 205/775 |

FOREIGN PATENT DOCUMENTS

| | | |
|---|---|---|
| EP | 1672364 A1 | 6/2006 |
| JP | 4 223257 A | 8/1992 |
| JP | 4223257 A | 8/1992 |
| WO | WO 2005/057168 A2 | 6/2005 |

\* cited by examiner

BIOSENSOR AND METHODS FOR MANUFACTURING

FIELD

Embodiments of this invention relate generally to biosensors for detecting an analyte in a fluid sample.

BACKGROUND

In many fields of healthcare, repeated measurement and monitoring of certain analytes present in bodily fluids, such as blood or urine, is of particular importance. A bodily fluid sample may be analyzed for a variety of properties or components, as is well known in the art. For example, such analysis may be directed toward hematocrit, coagulation, lead, iron, cholesterol, triglycerides, lactate, pyruvate, alcohol, uric acid, etc. One special case concerns, for example, patients affected by diabetes who need to measure the concentration of blood glucose very frequently in order to respond promptly with the correct medication. Exceeding certain blood glucose limits can result in coma or death. Even mildly elevated levels of blood glucose can result in gradually deteriorating health requiring long term monitoring to keep glycemic levels under control. As such, blood glucose data are useful to the physician who has the task to determine the most appropriate long-term therapy and to the patient who daily needs to adapt the administration of medications according to the measured glucose levels, which depend not only on diet, but also on daily physical activity and other factors that influence the patient's metabolism.

A number of small, reliable and low-cost medical devices, which can be handheld, are available today to the patient for self monitoring. Devices for controlled administration of therapeutic agents, such as insulin pumps, are also commercially available. The number of exemplary medical devices to which this invention refers to is, however, not limited to diabetes care. Worth mentioning are, for example, those devices for monitoring blood pressure or other blood parameters like coagulation factors and cholesterol.

Many medical devices available today include attaching a disposable test element to a reusable test meter with a sliding contact where the connector in the test meter slides along the test element, the test element contact, or both as the test element is inserted and removed from the test meter. However, these sliding contacts frequently result in the removal of material from the test element, such as by plowing or scraping, as the test element is inserted and removed from the test meter, although material may also be removed from the test meter. The removed material can build-up over time as numerous test elements are inserted and removed from a test meter affecting the proper operation of the system.

Additional complications can arise during the manufacture, storage or use of currently available test elements that are relatively thin and easily damaged while being handled.

Further complications can arise with the use of the typical medical devices when a patient or user suffers from poor eyesight or unsteady hands. These conditions might exist, for example, due to a congenital defect, a trauma, or an abnormal concentration of glucose in the blood, especially if the abnormal glucose concentration occurs over long periods. In other words, diabetic patients frequently suffer from visual impairment or a lack of fine motor skills, such as hand tremors.

It was realized by the inventors that improvements in biosensors are needed. For example, it was realized that improvements are needed in the connections between test elements and test meters, the durability of test elements, the ability to efficiently produce test elements, and a user's ability to dose a test element correctly. Certain features of the disclosed embodiments address these and other needs and provide other important advantages.

SUMMARY

Embodiments of the present invention provide an improved biosensor and methods for manufacturing.

In accordance with a first aspect of embodiments of the present invention, a biosensor, for example a test element, is provided comprising a plurality of embedded conductors in a substrate for electrochemically testing a fluid sample for an analyte. In one refinement, the embedded conductors comprise two or more wires supported within an elongated substrate having opposite ends, wherein each wire extends generally from one end to the other end, and is exposed or otherwise accessible at each end. In another refinement, one end of the test element is covered with a reagent configured for an electrochemical analysis of a fluid sample. The other end of the test element is configured for attachment to a test meter. In yet another refinement, the embedded conductors help stiffen and/or strengthen the test element. With such added stiffness/strength, the test element is generally more robust during further manufacturing processes, packaging, distribution/shipment, and use by a consumer. For example, the reagent can be applied with greater force and/or at higher temperatures than most conventional test elements.

Electrochemical test elements are generally provided with an electrode array comprising a working electrode and a counter and/or reference electrode. At least a portion of the electrode array, typically at least the working electrode, is coated, covered or otherwise in contact with a reagent layer. Each electrode is electrically connected, such as by an electrical lead or lead trace, to a distinct contact configured for engaging an electrical connector in a corresponding test meter with which the test element is provided for performing the electrochemical analysis. In certain aspects of the present invention, the embedded conductors comprise the electrodes, leads and contacts, and are electrically insulated from each other by the supporting substrate. The exposed portion of each conductor at each end of the test element comprises the contact and electrode, respectively, and the portion of the conductor extending between the ends of the test element comprise the lead electrically connecting therebetween.

In one form of the invention, the test meter comprises electrical connectors and the test element comprises electrical contacts, for connecting the test element and the test meter. The contacts on the test element can be arranged such that the rotational orientation of the test element about its longitudinal axis is irrelevant to the predetermined function of each conductor in the electrochemical analysis, allowing for a variety of test element geometric profiles. That is, although connectors in a meter typically correspond to pre-determined functionality based on the configuration of the electrical circuitry and programming of the test meter, the embedded conductors may be provided to be generally identical and arranged within the test element such that the functionality of each conductor depends only on which connector of the test meter it connects to when inserted therein; the functionality is thus irrelevant and unrelated to the position of each conductor within the test element.

Embodiments of the orientationally independent refinement of this aspect of the present invention include test elements that are generally cylindrical with various cross-sectional shapes or profiles, and test element receptacles on test meters having complimentary shapes or profiles for receiving such test elements. Examples of cross-sectional shapes or profiles for test elements include circular, elliptical, ovoid, square, rhombic, rectangular, triangular, trapezoidal, and other suitable polygonal shapes such as pentagonal, hexagonal and octagonal.

In another refinement, the conductors are embedded in functionally dependent positions within the test element substrate, and the meter connectors, rather than being functionally predetermined, are functionally adjustably configured with the circuitry and programming of the meter depending on the detected positions of the conductors of an inserted test element. Once the test element is placed in the appropriately shaped receptacle and the test element electrodes are detected by the test meter, the test meter's software can detect the test element's orientation and perform an appropriate analysis, assigning functionality of the meter connectors based on the detected positions of the conductors. In other words, the meter can map the connections between the connectors and contacts of the test elements, wherein the test element cannot be inserted upside down. Alternatively or additionally, registration marks and/or detents can be formed, such as by crimping or scoring the initially soft plastic during, for example, the cutting process. The registration marks and/or detents can be used to hold the test element and/or lock the orientation of the test element within the meter, such as by a key registration.

Embodiments of the present invention generally include non-sliding connection between the test element and the test meter, which reduces or eliminates the scraping or plowing of material as the test elements are inserted into and removed from the test meter. This, in turn, can reduce or eliminate the accumulation of debris, such as the plastic of the supporting substrate (e.g. Melinex brand polymer) or the metal of the contact end of the conductor (e.g. gold or copper), inside the test meter. In embodiments where the test element is not substantially flat, for example test elements formed into circular or hexagonal columns, the surface area of the dosing area can be increased while minimizing the volume of the disposable. A test element profile in the form of a circular cylinder, or other similar structure, can help to assure uniform dosing occurs across the end of the test element. Still further embodiments include using the test elements as non-capillary flow biosensors or including other capillary-like structures with the test element for retaining the fluid sample on the reagent.

In still other aspects of other embodiments, test elements can be formed by, for example, pultruding electrical conductors through a resin, such as a polymeric matrix, and cutting the length of pultruded material to the desired length, exposing the individually insulated electrical conductors on the ends of the elements, and applying a reagent to one end, i.e. the electrode end, where the electrical conductors are exposed.

In aspects of still further embodiments, the test elements include reagents that are adapted to test for blood glucose, and the reagents can include, for example, glucose dehydrogenase or glucose oxidase. In still further aspects of other embodiments, the test elements include reagents adapted to test for other properties or components of bodily fluid, such as hematocrit, coagulation, lead, iron, cholesterol, triglycerides, lactate, pyruvate, alcohol, uric acid, etc..

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not intended to address every object described herein, and each embodiment does not necessarily include each feature described. Other forms, embodiments, objects, advantages, benefits, features, and aspects of the present invention will become apparent to one of skill in the art from the detailed description and drawings contained herein.

DETAILED DESCRIPTION OF THE ILLUSTRATED EMBODIMENTS

For the purposes of promoting an understanding of the principles of the invention, reference will now be made to the selected embodiments illustrated in the drawings and specific language will be used to describe the same. It will nevertheless be understood that no limitation of the scope of the invention is hereby intended, such alterations, modifications, and further applications of the principles of the invention being contemplated as would normally occur to one skilled in the art to which the invention relates. At least one embodiment of the invention is shown in great detail, although it will be apparent to those skilled in the relevant art that some features or some combinations of features may not be shown for the sake of clarity.

Figure 1:
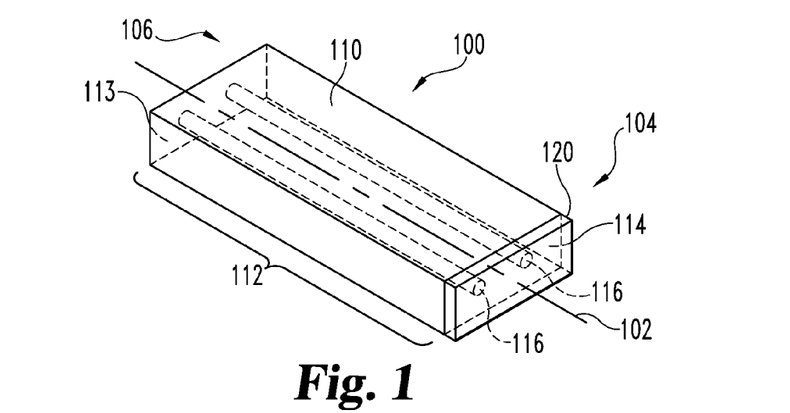
FIG. 1 is a perspective view of a biosensor according to one embodiment of the present invention.
Figure 2:
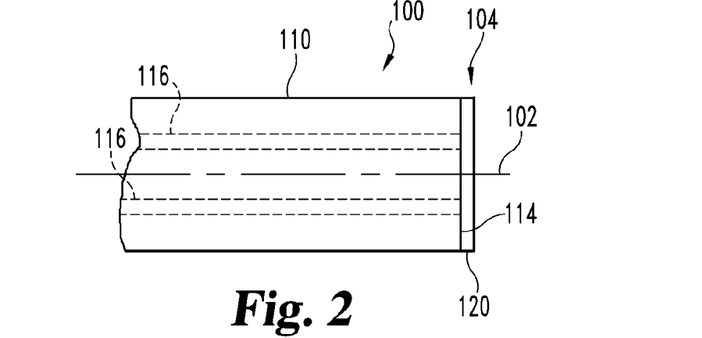
FIG. 2 is a top plan view of the biosensor depicted in FIG. 1.
Figure 3:
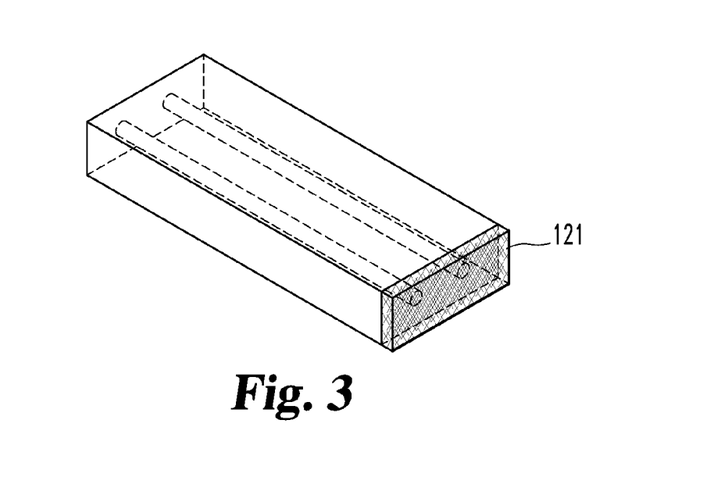
FIG. 3 is a perspective view of a biosensor according to a further embodiment of the present invention.

Depicted in FIGS. 1 and 2 is a biosensor, for example test element 100, according to one embodiment of the present invention. Test element 100 defines a longitudinal axis 102 and includes a single-piece test element body 110 and reagent layer 120. Test element body 110 defines a length 112 along longitudinal axis 102 and includes at least two electrical conductors capable of supporting electrical communication between its ends, for example generally rigid rods or wires 116, extending along its length from end surface 113 to end surface 114. Wires 116 are embedded within the single-piece test element body 110 and are exposed at end surfaces 113 and 114.

As used herein, a single-piece body may be formed from separate portions, but in its final configuration is a single piece. For example, a single-piece body may be a body formed of continuous and homogeneous material, such as a supporting substrate, or a single-piece body may be a body formed by fusing at least two objects together. In one form, a single-piece body is a body formed around an electrical conductor that has been pulled through a thermoplastic or thermal setting resin that is subsequently dried, cooled or cured, such as through a pultrusion process.

Because they are embedded within the strip body, wires 116 are generally protected and electrically insulated along their length. As such, the need for a protective laminate layer such as is frequently applied to cover the electrodes of traditional test elements is eliminated. At end surface 114, exposed portions of wires 116 are coated with or otherwise contacted with a reagent, for example, reagent layer 120. When wetted with a sample fluid, reagent layer 120 is in electrical communication with the portions of wires 116 exposed to the reagent layer 120. In one embodiment, reagent layer 120 comprises a carrier, such as a mesh 121, that carries or is coated with the reagent, and which is adhered or otherwise mounted to the end surface 114.

Test element 100 further includes test end 104 and test meter connection end 106. Test end 104 is adapted to receive a sample of fluid for testing and includes reagent layer 120. Users with impaired eyesight or impaired manual dexterity will frequently find it easier to properly apply a sample to the end of a test element since the location for applying the sample is easily identified. Test meter connection end 106 is adapted to connect to a test meter and electrically communicates with test end 104 via wires 116. The presence and/or concentration of an analyte present in a sample of fluid may be determined when the sample of fluid is applied to test end 104 and the test meter connection end 106 is connected to a test meter.

The electrical conductors provide sufficient electrical conductivity to connect the test end 104 to a test meter and may be formed of various conductive materials, for example, copper, gold and palladium. Test element body 110 provides sufficient insulation between the electrical conductors and the environment outside the biosensor to insure proper operation of the test element and its ability to communicate with the test meter. Test element body 110 may be formed of a polymeric matrix, for example, polyethylene terephthalate (such as, e.g., Melinex brand polymer substrate material), polybutyl terephthalate, or other similar materials capable of use in a pultrusion manufacturing process and providing sufficient electrical insulation for the operation of the test element.

In one embodiment, the reagent layer 120 is adapted to test for glucose, such as determining the presence or concentration of glucose in a sample of body fluid, for example, blood. For example, in certain embodiments reagent layer 120 is adapted to test for the presence or concentration of glucose in a sample of bodily fluid, such as blood and may include, for example, glucose dehydrogenase or glucose oxidase. In still other embodiments, the reagent layer 120 is adapted to test for other properties or components of bodily fluid, such as hematocrit, coagulation, lead, iron, cholesterol, triglycerides, lactate, pyruvate, alcohol, uric acid, etc. Furthermore, although reagent layer 120 is depicted as covering the end of test element body 110, alternate embodiments include reagent layers that do not completely cover an end of the test element body provided that the reagent amount and location is sufficient for testing a sample of body fluid.

Figure 4:
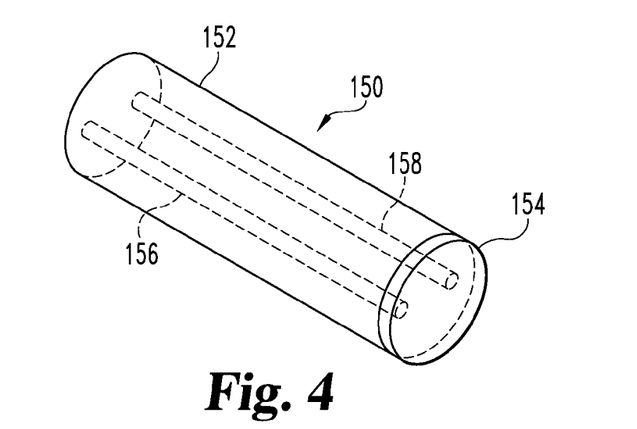
FIG. 4 is a perspective view of a biosensor according to another embodiment of the present invention.

In one embodiment, test element 100 is generally cylindrical in shape with a rectangular cross-section, although alternate embodiments of the present invention include test elements having alternatively-shaped cross sections, such as cylindrical columns with triangular, elliptical, hexagonal, square or circular cross-sections. For example, FIG. 4 depicts a test element 150 in the form of a circular cylinder according to another embodiment of the present invention. Test element 150 includes a single-piece test element body 152 and reagent layer 154 affixed to one end of test element body 152. Embedded within the illustrated test element body 152 are electrical conductors 156 and 158.

When connected to a test meter, one of the wires 116 will perform as a working electrode while the other wire 116 performs as a counter electrode. In the embodiment illustrated in FIGS. 1 and 2, wires 116 are symmetrically arranged within test element body 110, which allows test element 100 to be inserted into the test meter as depicted in FIG. 1 or inserted into the test meter in an orientation that is rotated 180 degrees around longitudinal axis 102 (flipped upside down) before being inserted into the test meter. As such, it is easier for a user to insert test element 100 into a meter than to insert traditional test elements into a meter since traditional test elements are typically sensitive to orientation and cannot be inserted upside down.

Figure 5:
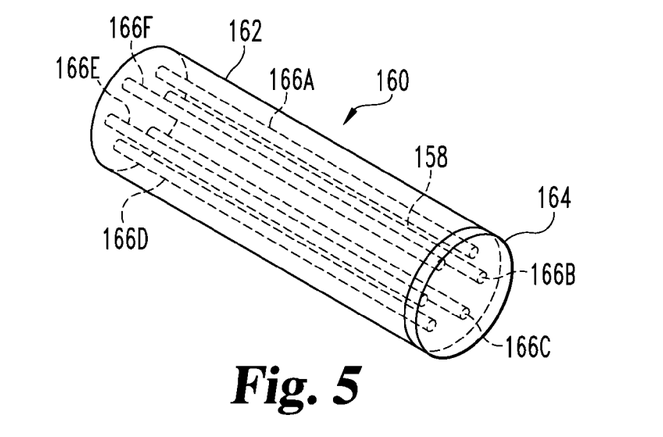
FIG. 5 is a perspective view of a biosensor according to still another embodiment of the present invention.

Depicted in FIG. 5 is a test element 160 according to still another embodiment of the present invention. Similar to test element 150, test element 160 resembles a circular cylinder and includes a cylindrical test element body 162 with a circular cross-section and a reagent layer 164 affixed to one end of test element body 162. Embedded within test element body 162 are wires 166A, 166B, 166C, 166D, 166E and 166F. The wires 166A-F may perform different functions in test element 160. For example, in one embodiment wire 166A is a working electrode while wire 166D is a counter-electrode and wires 166B, 166C, 166E and 166F are dose detection and sample volume sufficiency electrodes.

Wires 166 are embedded in a generally symmetrical orientation. As such, there is generally no need to pre-assign or predetermine the functions of wires 166 prior to inserting test element 160 into a test meter. Rather, in one embodiment of the present invention, the corresponding meter connectors function according to the electrical circuitry and/or programming of the meter. Because all of the wires 166 are generally identical in this embodiment, the function of any particular wire 166 depends upon the test meter connector with which the particular wire 166 makes contact.

Figure 6:
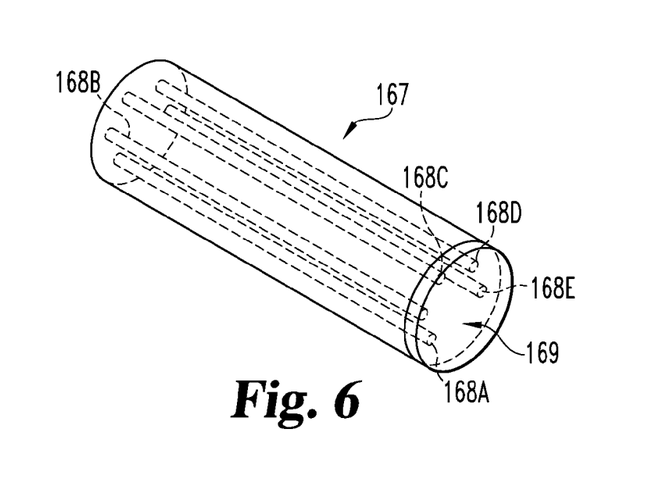
FIG. 6 is a perspective view of a biosensor according to yet another embodiment of the present invention.
Figures 12, 13, 14, 15:
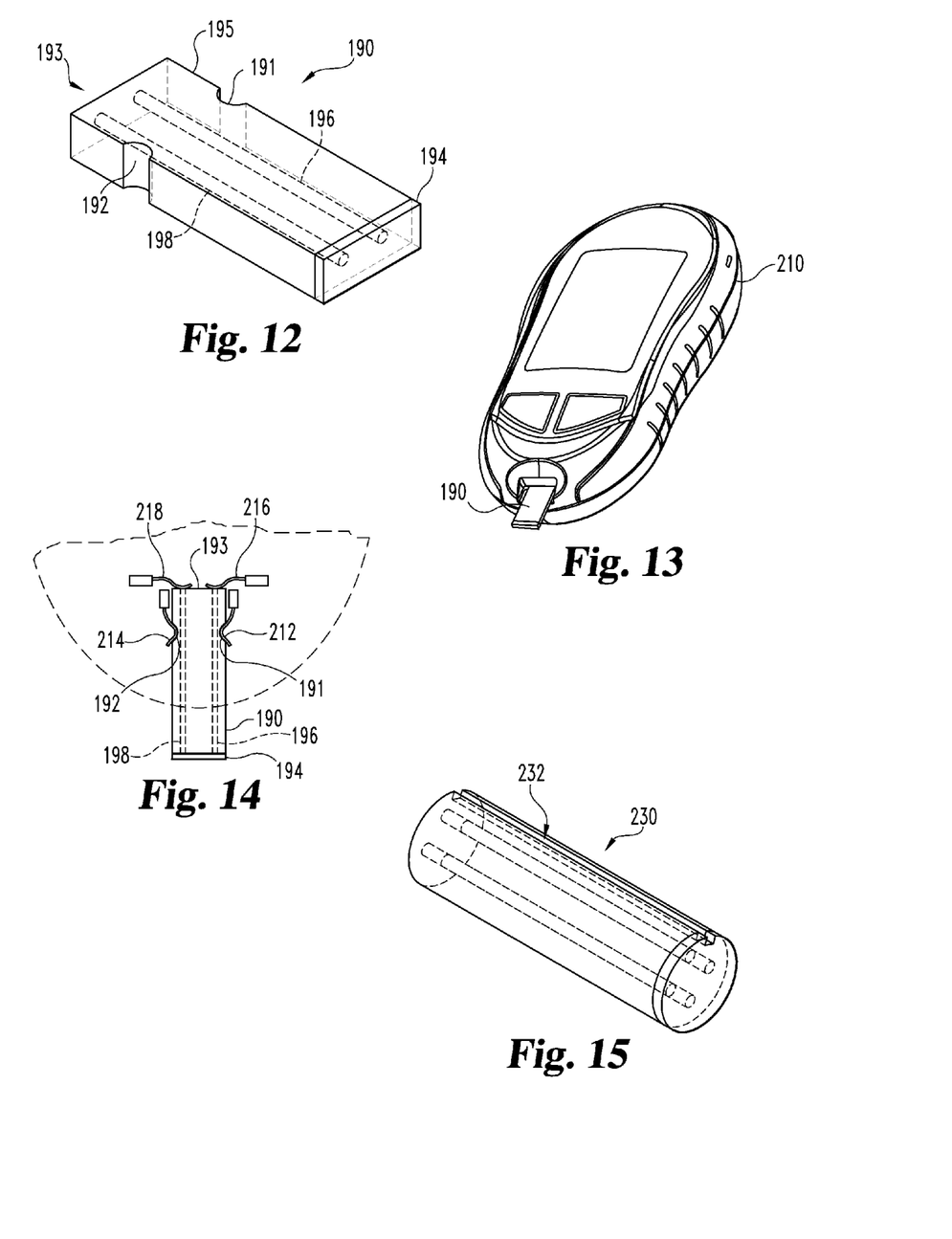
FIG. 12 is a perspective view of a biosensor according to still a further embodiment of the present invention.
FIG. 13 is a perspective view of a test element connected to a test meter according to one embodiment of the present invention.
FIG. 14 is a partial, top plan view of the test element and test meter depicted in FIG. 13.
FIG. 15 is a perspective view of a biosensor according to yet another embodiment of the present invention.

In alternate embodiments, the test element includes an asymmetrical orientation of electrical conductors, for example, wires. For example, test element 167 depicted in FIG. 6 includes asymmetrically arranged wires 168-168A, 168B, 168C, 168D and 168E. In one alternative, the test meter into which test element 167 is inserted, which can resemble the test meter 210 in FIG. 13, is adapted to discern the orientation of the test element 167 and adjust the functionality of the test meter connectors accordingly. In the example depicted in FIG. 6, the five (5) wires 168A-168E are positioned within five (5) of six (6) potential wire locations in test element 167. The unfilled location 169 is blank and contains no wire—no conductor is provided at location 169. The test meter into which test element 167 is inserted includes, for example, six (6) connectors corresponding to the six (6) potential locations of the test element wires. When test element 167 is inserted into the test meter, the meter detects an electrical change, such as a drop in electrical potential, at only five (5) of the six (6) connectors, which indicates the orientation of the test element. The programming in the meter then assigns functionality to the connectors according to the desired function. For example, in a first orientation the test meter can assign a connector the functionality of a working electrode and operate the connector as a working electrode connector, and in a second orientation the test meter can assign a connector the functionality of a counter electrode and operate the connector as a counter electrode connector. In this manner, the orientation of the test element 167 determines the functionality of the test meter's connectors.

As another example, at least one of the test element electrical conductors, for example, one of the wires 168 in test element 167 (FIG. 6) or one of the wires 166 in test element 160 (FIG. 5), is constructed of different materials than at least one of the remaining test element conductors, resulting in an asymmetric arrangement of wire types within the test element. For example, at least one of the wires is copper while at least one of the remaining wires is gold. By detecting the difference between the wires, a test meter adapted to receive the test element discerns the orientation of the test element and adjusts the functionality of the test meter connectors according to the desired function and consistent with, for example, the system parameters relating to a copper electrode versus a gold electrode.

Figure 7:
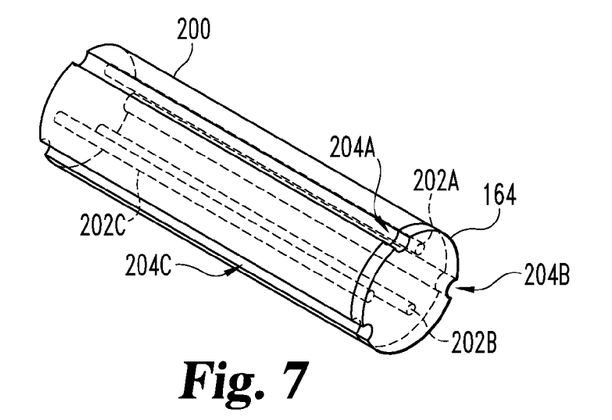
FIG. 7 is a perspective view of a biosensor according to still a further embodiment of the present invention.
Figure 8:
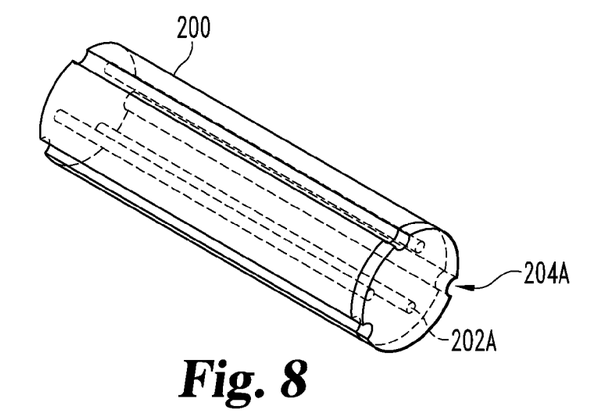
FIG. 8 is a perspective view of the biosensor depicted in FIG. 7 in a different rotational orientation.
Figure 9:
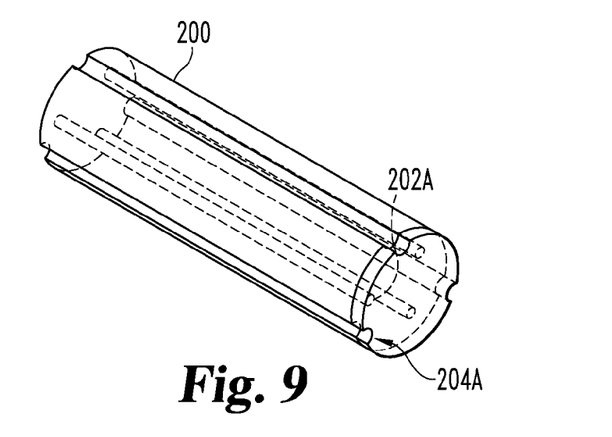
FIG. 9 is a perspective view of the biosensor depicted in FIGS. 7 and 8 in a still different rotational orientation.

In an alternative embodiment, rather than configuring the meter to detect the orientation of a strip having asymmetrically embedded conductors or even symmetrically embedded conductors having variable characteristics (e.g. copper versus gold), the connection between the test element and the test meter is adapted to permit connection between the test element and the test meter only when the test element is in one or more particular orientations. For example, test element 200 depicted in FIGS. 7, 8 and 9 includes at least one recess, such as a scoring or a groove, for example grooves 204A, 204B and 204C, and wires 202A, 202B and 202C. The test meter, which may be similar to test meter 210 in FIG. 13, is adapted to receive test element 200 and includes at least one extended portion that is complementary to the at least one recess on test element 200. For proper insertion into the test meter, test element 200 will be in one of the three orientations depicted in FIGS. 7, 8 and 9. See also, e.g., FIGS. 8 and 13.

Of note with regard to test elements having various cross-sectional profiles (for whichever of the purposes described herein), the connectors provided in a corresponding meter typically are provided in a receptacle of the meter configured to receive the particular test element. For example, a test element having a rectangular cross-sectional profile will frequently be inserted into a meter having a rectangular receptacle wherein the connectors are provided for electrical connection to the test element. See, e.g., FIGS. 12-14. Alternative test element profiles can correspond similarly to meter receptacles of complimentary receiving profiles.

Figure 10:
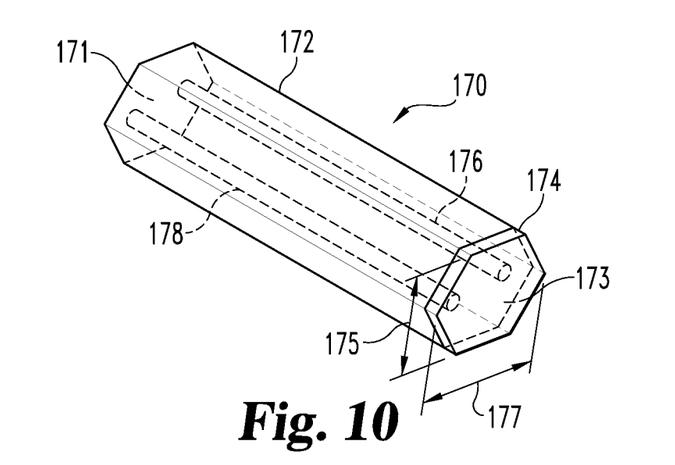
FIG. 10 is a perspective view of a biosensor according to another embodiment of the present invention.

Depicted in FIG. 10 is a test element 170 according to yet another embodiment of the present invention. Test element 170 is cylindrical in shape with a hexagonal cross-section. Test element 170 includes a test element body 172 with end surfaces 171 and 173, and a reagent layer 174 affixed to end surface 173. The height 175 and width 177 of test element 170 are approximately equal. Embedded within test element body 172 are wires 176 and 178, which are exposed at end surfaces 171 and 173. The hexagonal shape of the test element 170 can have advantages during packaging since the hexagonal elements will self-orient as they are packaged and the test elements 170 will rest firmly against one another with little or no gaps between the test elements.

Another advantage of a polygonal shape is its ability to inherently align the test element contacts with the connectors of the test meter. That is, although embodiments of the present invention provide at least some degree of orientational independence, electrical contact between the test element and the test meter still must be made in order for the system to operate properly. As such, embodiments of the present invention include test elements with polygonal cross-sectional shapes (or other alignment-selective cross-sectional shapes) and test meters with complimentarily shaped test elements receptacles to ensure that the test elements contact(s) align with the test meter connector(s) when the test element is inserted into the test meter.

Figure 11:
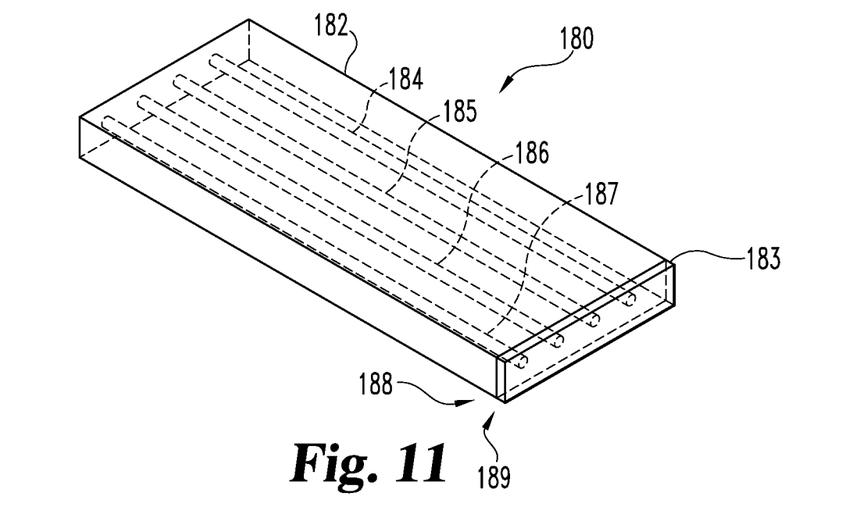
FIG. 11 is a perspective view of a biosensor according to yet a further embodiment of the present invention.

Turning to FIG. 11, a test element 180 according to still a further embodiment of the present invention is depicted. Test element 180 includes test element body 182 and reagent layer 183. Embedded within test element body 182 are conductive wires 184, 185, 186 and 187. When connected to a test meter, conductive wires 184-187 connect the test circuitry in the test meter to the test area 188 at test end 189. Depending on the circuitry in the test meter, the conductive wires 184-187 can perform different functions. For example, in one embodiment, conductive wires 184 and 187 function as dose sufficiency electrodes, wire 185 functions as a working electrode, and wire 186 functions as a counter electrode when test element 180 is connected to a test meter. In another alternative, test element can be inserted into a test meter in an orientation that is upside-down to that depicted in FIG. 11, with wire 185 functioning as a counter electrode and wire 186 functioning as a working electrode.

It can be useful to positively hold one of the biosensors within the test meter during use. Test element 190, depicted in FIG. 12, includes a test element body 195, a reagent layer 194, conductive wires 196 and 198 and detents 191 and 192. Detents 191 and 192 are formed into test element body 195 and are useful for positively holding test element 190 within a test meter.

FIGS. 13 and 14 depict test element 190 inserted into a test meter 210 according to one embodiment of the present invention. Test meter 210 includes connectors, for example spring retention clips 212 and 214, which connect to test element detents 191 and 192, respectively. Retention clips 212 and 214 are generally complementary in shape to detents 191 and 192.

Test meter 210 further includes electrical connectors 216 and 218 that electrically connect to conductive wires 196 and 198, respectively. As test element 190 is inserted into test meter 210, retention clips 212 and 214 deflect outwardly while maintaining an inward pressure on test element 190. Once the test element is inserted a sufficient distance, retention clips 212 and 214 register with detents 191 and 192 and maintain positive pressure on test element 190 to retain test element 190 within test meter 210.

As retention clips 212 and 214 are fully registering with detents 191 and 192, the connection end 193 of test element 190 contacts electrical connectors 216 and 218. With the retention clips 212 and 214 fully registered with detents 191 and 192, the conductive wires 196 and 198 contact the electrical connectors 216 and 218 making an electrical connection between clips 212/214 and conductive wires 196/198. Electrical connectors 216 and 218 are arranged to minimize the movement, for example the sliding, of electrical connectors 216 and 218 across the surface of test element 190. In one embodiment, electrical connectors 216 and 218 move at most one millimeter (1 mm) across the surface of test element 190. In another embodiment, electrical connectors 216 and 218 move at most one-half millimeters (0.5 mm) across the surface of test element 190. In still another embodiment, electrical connectors 216 and 218 move at most one-tenth millimeters (0.1 mm) across the surface of test element 190. And in still a further embodiment, electrical connectors 216 and 218 and the test element connect in a non-sliding manner where the electrical connectors 216 and 218 do not move across the surface of test element 190. Minimizing the movement of the electrical connectors across the wires minimizes the scraping or plowing that occurs when typical test elements are inserted into a test meter. As such, the amount of material that is scraped off of the test elements as they are inserted and removed from the test meter is minimized or eliminated, and the difficulties associated with a build up of excess scraped-off material that can affect the performance of the test meter over time is minimized or eliminated. Additionally, the careful balancing of contact forces between the test element and test meter to prevent plowing of the electrical contact tabs and test element material with the insertion and extraction of typical elements from test meters is eliminated, or at least minimized.

In the embodiment illustrated in FIG. 14, test element 190 contacts electrical connectors 216 and 218 before detents 191 and 192 fully register with retention clips 212 and 214. As such, electrical connectors 216 and 218 deflect from their resting positions and maintain positive pressure on test element 190 while test element 190 is fully registered with retention clips 212 and 214. In alternate embodiments, there is little or no deflection of electrical connectors 216 and 218 while test element 190 is fully registered with retention clips 212 and 214, resulting in a negligible amount of pressure being applied by electrical connectors 216 and 218 to test element 190.

Electrical connectors 216 and 218 can be arranged such that the rotational orientation of the test element about its longitudinal axis does not affect the operation of the test element. For example, in one embodiment of the present invention the electrical connectors are arranged such that when a test element with a hexagonal profile, such as the one depicted in FIG. 10, is inserted into the test meter, the test element will operatively connect to the test meter in the six possible rotations.

As another example, the electrical connectors in the test meter may be arranged such that a test element with a circular cross-section, such as the one depicted in FIG. 4, can be inserted in any rotational orientation and still operatively connect with the test meter.

As a further example, the outer surface of a test element, such as the test element 230 with a generally-circular cross-section (FIG. 15), may include registration elements, such as at least one longitudinal score or groove 232, that match corresponding registration elements on the test meter, such as at least one protrusion, for example a boss, to aid in aligning the test element within the test meter. When test element 230 is inserted into the test meter, the groove 232 and its corresponding boss in the test meter help ensure that the test element 230's electrical contact(s) properly engage the connector(s) in the meter. It should be appreciated that the scores or grooves may be included in the test meter receptacle and the complimentary bosses may be included in the test element.

In still other embodiments, the electrical circuitry and/or software in the test meter decodes the orientation of the test element when the test element is inserted into the test meter. As such, the orientation of the test element can be used for encoding purposes or to detect possible errors in orientation.

In one embodiment, the wires are made from inexpensive conductive materials, such as copper, and the ends of the wire near the reagent are pressed, plated, sputtered, and/or otherwise coated with a noble metal, for example palladium, silver, platinum and gold, or other inert conductive material to prevent contamination of the reagent with the copper. This construction in turn can reduce the materials cost for the resulting test element.

Figure 16:
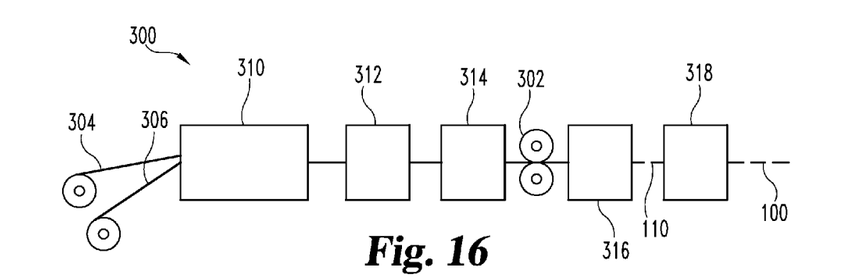
FIG. 16 is a graphical depiction of a manufacturing processing according to one embodiment of the present invention.

A process for manufacturing a biosensor, for example test element 100, according to one embodiment of the present invention is depicted in FIG. 16. Process 300 includes a pulling mechanism 302 that pulls the elemental components that form the test element though one or more process stations. For example, pulling mechanism 302 pulls a first electrical conductor 304 and a second electrical conductor 306 through a resin bath 310. After the electrical conductors 304 and 306 pass through the resin bath 310, the resin is set at the curing station 312. For example, the resin applied to electrical conductors 304 and 306 in the resin bath 310 may be a thermal set resin that undergoes polymerization, such as by cross-linking polymer components, by the application of heat or ultraviolet light in curing station 312. Alternatively, station 312 is a drying station, wherein the resin comprises thermoplastic components. The cured or dried resin and the electrical conductors 304 and 306 are then shaped into their final form at shaping station 314. Shaping includes forming the cross-sectional profile of the cylindrical form, as well as forming any detents, scores, grooves, or other key or external alignment identifiers and/or retention means. The shaped material 108 is then cut into segments by cutter 316. The individual segments are test element bodies, for example, test element bodies 110. Reagent is then applied to the individual segments at reagent application station 318, thereby forming one or more test elements 100.

Figure 17:
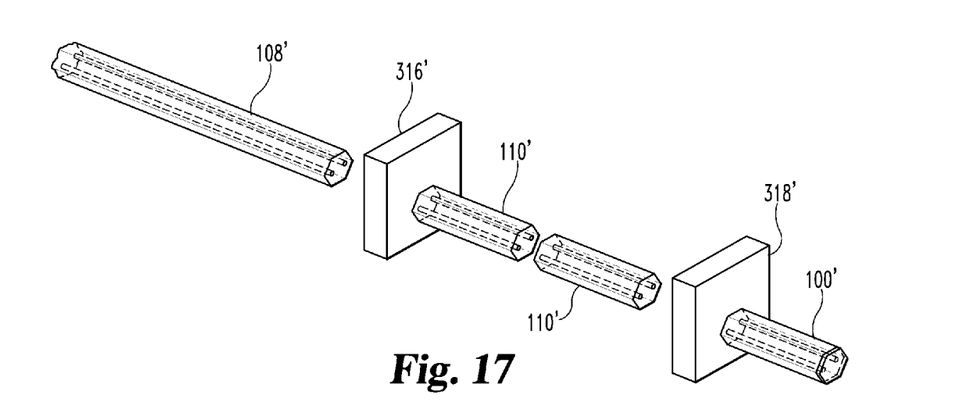
FIG. 17 is a perspective view of one example embodiment of the manufacturing process depicted in FIG. 16.

An example of process 300 is depicted in FIG. 17. In FIG. 17, the shaped material 108' entering cutter 316' is generally hexagonal in cross-section with two embedded electrical conductors. Similarly, test element bodies 110' entering reagent application station 318' and the test elements 100' exiting reagent application station 318' are generally hexagonal in cross-section with two embedded electrical conductors.

Process 300 is one form of a pultrusion process and other similar processes are also contemplated within the scope of the present invention. For example, one or more of the stations 310, 312, 314, 316 and 318, which are depicted as being separate in FIG. 16, may be combined, such as the curing and shaping functions may be performed simultaneously or nearly simultaneously at a single station.

Figure 18:
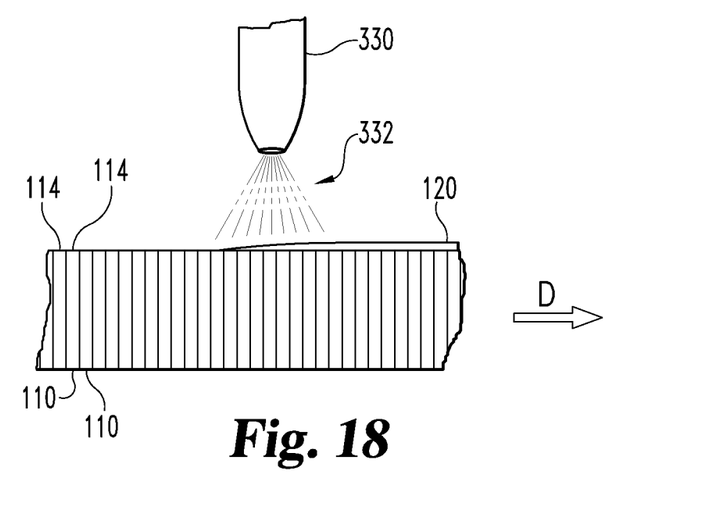
FIG. 18 is a side elevational view depicting the application of a reagent to a plurality of biosensors according to one embodiment of the present invention.

As depicted in FIG. 16, process 300 comprises the sequential application of reagent to a plurality of test element bodies, for example test element bodies 110, as the test element bodies pass through the reagent application station 318. However, other embodiments contemplate alternate methods for applying reagent to a plurality of test element bodies 110. For example, FIG. 18 depicts a plurality of test element bodies 110 arranged in a closely-spaced grouping with end surfaces 114 positioned adjacent one another, where the test element bodies 110 travel in direction D past a sprayer 330. As the test element bodies 110 pass sprayer 330, sprayer 330 simultaneously applies a spray 332 of reagent to a plurality of test element bodies 110 to form reagent layer 120.

Figure 19:
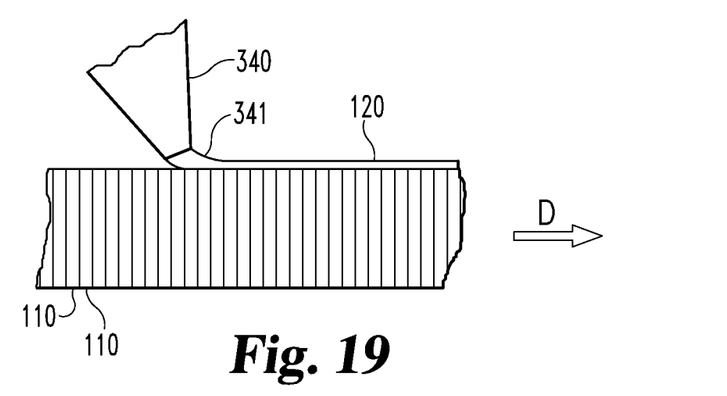
FIG. 19 is a side elevational view depicting the application of a reagent to a plurality of biosensors according to another embodiment of the present invention.

Depicted in FIG. 19 is another process for applying a reagent layer to a plurality of test element bodies according to another embodiment of the present invention. A plurality of test element bodies 110 are arranged in closely-spaced adjoining relation to one another and move in a direction D past an applicator 340 that applies reagent material 341 to the plurality of test element bodies 110 to form reagent layer 120.

Process 300 can be run as a continuous production process and can produce a large number of test elements in a relatively short time. Additionally, pultruding the electrical conductors through a polymeric matrix protects the electrical conductors from damage. Furthermore, the presence of the electrical conductors within the polymeric matrix can result in test elements that resist bending more than traditional test elements. As such, the durability and robustness of the test element body is more resistant to damage during manufacture than traditional test elements.

Process 300 is also easily scaleable between very thick or very fine electrical wires. As such, the size of the electrical wires may be scaled for higher or lower electrical current requirements as necessary.

Alternate techniques for manufacturing biosensors can also be used to produce biosensors with electrical conductors extending from one end of an electrically insulating test element body coated with reagent to another end of the test element body that connects with a test meter as described herein. For example, extrusion-type processing methods may be used to form biosensors as disclosed herein.

While illustrated examples, representative embodiments and specific forms of the invention have been illustrated and described in detail in the drawings and foregoing description, the same is to be considered as illustrative and not restrictive or limiting. The description of particular features in one embodiment does not imply that those particular features are necessarily limited to that one embodiment. Features of one embodiment may be used in combination with features of other embodiments as would be understood by one of ordinary skill in the art, whether or not explicitly described as such. Dimensions, whether used explicitly or implicitly, are not intended to be limiting and may be altered as would be understood by one of ordinary skill in the art. Exemplary embodiments have been shown and described, and all changes and modifications that come within the spirit of the invention are desired to be protected.

What is claimed is:

1. A biosensor adapted to detect an analyte in a body fluid sample, comprising:
   a single-piece, electrically-insulating, elongated body having a uniform, alignment-selective, cross-sectional shape throughout its length, and having a first orthogonal end surface at a first end of the body and a second orthogonal end surface at the second end of the body, the alignment-selective, cross-sectional shape constituting a body registration feature for orienting said body in a predetermined position relative to a receptacle in which said body is placed;
   at least two electrical conductors embedded and electrically insulated completely along their length within the single-piece body and extending between the first and second end surfaces of the body, the at least two electrical conductors having exposed first end surfaces flush and coplanar with the first end surface of the body and exposed second end surfaces flush and coplanar with the second end surface of the body; and
   a reagent disposed on the exposed first end surfaces of the at least two electrical conductors, the reagent being configured to electrochemically react with a body fluid sample applied to the reagent, and wherein the reagent is in electrical communication with the electrical conductors when the body fluid is applied to the reagent.

2. The biosensor of claim 1, wherein the single-piece body has a cross-sectional shape generally comprising one of the shapes selected from the group consisting of ovoid, elliptical, hexagonal, square, rectangular, pentagonal, octagonal and triangular.

3. The system of claim 2 in which the body registration feature comprises the body having a cross-sectional shape other than round, and the meter registration feature comprises the receptacle defining a cavity complementary in shape to the cross-sectional shape of the body.

4. The biosensor of claim 1, wherein the single-piece body has a regular or irregular polygonal cross-sectional shape.

5. The biosensor of claim 1, wherein the reagent comprises at least one enzyme adapted to test for blood glucose.

6. The biosensor of claim 1 wherein the body is formed from a thermoplastic or thermosetting resin.

7. The biosensor of claim 1 wherein the body is formed from by pultrusion.

8. A system for detecting an analyte in a sample of body fluid, comprising:
   a biosensor comprising a single-piece, electrically-insulating, elongated body having a uniform, alignment-selective, cross-sectional shape throughout its length, and having a first orthogonal end surface at a first end of the body and a second orthogonal end surface at the second end of the body, the alignment-selective, cross-sectional shape constituting a body registration feature for orienting said body in a predetermined position relative to a receptacle in which said body is received, at least two electrical conductors embedded and electrically insulated completely along their length within the body and extending between the first and second end surfaces of the body, the at least two electrical conductors having exposed first end surfaces flush and coplanar with the first end surface of the body and exposed second end surfaces flush and coplanar with the second end surface of the body, a reagent being disposed on the exposed first end surfaces of the at least two electrical conductors; and
   a test meter comprising a receptacle configured to receive the bio sensor, the receptacle defining an opening shaped complementary with the cross-sectional shape of the body, the body being received within the opening of the receptacle and thereby being oriented in a predetermined position relative to the receptacle, the receptacle further including at least two electrical connectors adapted to electrically connect with the second end surfaces of the electrical conductors when the second end of the body is inserted into the receptacle.

9. The system of claim 8, wherein the electrical connectors connect with the surface of the bio sensor in a non-sliding manner.

10. The system of claim 8, wherein the electrical connectors slide at most one-half millimeter (0.5 mm) across the surface of the biosensor as the biosensor is connected to the test meter.

11. The system of claim 8, wherein the reagent comprises at least one enzyme adapted to test for blood glucose.

12. The system of claim 8, wherein the body has an outer surface comprising at least one detent, and wherein the receptacle comprises at least one retention clip corresponding to the at least one detent and configured to register with the at least one detent in order to retain the biosensor within the receptacle.

13. The system of claim 8, wherein the bio sensor includes a feature detectable by the test meter, and wherein the test meter detects the orientation of the bio sensor by detecting the location of the bio sensor feature.

14. The system of claim 13, wherein the bio sensor feature includes the at least two electrical conductors comprising different materials.

15. The system of claim 13, wherein the bio sensor includes a plurality of potential electrical conductor locations, and the feature includes the absence of an electrical conductor in at least one of the potential electrical conductor locations.

16. The system of claim 8, wherein the single-piece body has a regular or irregular, polygonal cross-sectional shape.

17. The system of claim 16, wherein the single-piece body has a cross-sectional shape generally comprising one of the shapes selected from the group consisting of ovoid, elliptical, hexagonal, square, rectangular, pentagonal, octagonal and triangular.

18. The system of claim 8 in which the body is formed of a continuous and homogeneous material.

19. The system of claim 8 in which the electrical conductors are symmetrically arranged.

20. The system of claim 8 in which the electrical conductors are asymmetrically arranged.

21. The system of claim 8 in which at least two of the electrical conductors are formed from different materials.

22. The system of claim 8 in which the body has an exterior surface including a continuous, uniformly-shaped groove extending the length of the body, and the receptacle includes an extended portion that is complementary to the groove.

23. The system of claim 8 wherein the body is formed from a thermoplastic or thermosetting resin.

24. The system of claim 8 wherein the body is formed from by pultrusion.

25. A bio sensor adapted to detect an analyte in a body fluid sample, consisting of:
   a single-piece, electrically-insulating, elongated body having a uniform, alignment-selective, cross-sectional shape throughout its length, and having a first orthogonal end surface at a first end of the body and a second orthogonal end surface at the second end of the body, the alignment-selective, cross-sectional shape constituting a body registration feature for orienting said body in a predetermined position relative to a receptacle in which said body is placed;
   at least two electrical conductors embedded and electrically insulated completely along their length within the single-piece body and extending between the first and second end surfaces of the body, the at least two electrical conductors having exposed first end surfaces flush and coplanar with the first end surface of the body and exposed second end surfaces flush and coplanar with the second end surface of the body; and
   a reagent disposed on the exposed first end surfaces of the at least two electrical conductors, the reagent being configured to electrochemically react with a body fluid sample applied to the reagent, and wherein the reagent is in electrical communication with the electrical conductors when the body fluid is applied to the reagent.

26. The biosensor of claim 25 wherein the body is formed from a thermoplastic or thermosetting resin.

27. The biosensor of claim 25 wherein the body is formed from by pultrusion.

* * * * *